United States Patent [19]

Malhotra et al.

[11] 4,006,111
[45] Feb. 1, 1977

[54] PRODUCTION OF ALKANE: OLEFIN SULFONATE MIXTURES BY SEQUENTIAL SULFONATION AND SULFITATION

[75] Inventors: Virender Nath Malhotra; John Mather, both of Wirral, England

[73] Assignee: Lever Brothers Company, New York, N.Y.

[22] Filed: July 11, 1973

[21] Appl. No.: 378,082

[30] Foreign Application Priority Data

July 12, 1972 United Kingdom ............ 36252/72

[52] U.S. Cl. ................................. 252/555; 252/174; 252/535; 252/536; 252/554; 252/DIG. 16; 260/513 R

[51] Int. Cl.[2] ............ C07D 139/12; C07D 143/16; C11D 1/14; C11D 1/37

[58] Field of Search .......... 252/535, 536, 554, 555, 252/174, DIG. 16; 260/513 R, 513 RS

[56] References Cited

UNITED STATES PATENTS

| | | | |
|---|---|---|---|
| 3,415,753 | 12/1968 | Stein | 252/121 |
| 3,423,453 | 1/1969 | Baumann | 260/513 R |
| 3,488,384 | 1/1970 | Kessler | 260/513 |
| 3,622,517 | 11/1971 | Norton | 252/544 |
| 3,652,662 | 3/1972 | Sweeney | 252/555 X |
| 3,676,374 | 7/1972 | Zaki | 252/535 X |
| 3,696,143 | 10/1972 | Malhorta | 252/554 X |
| 3,781,339 | 12/1973 | Tuvell | 260/513 R |
| 3,803,058 | 4/1974 | Marty | 252/555 X |
| 3,808,157 | 4/1974 | Dewitt | 252/555 |
| 3,812,060 | 5/1974 | Alsbury | 252/555 |
| 3,843,564 | 10/1974 | Marty et al. | |

FOREIGN PATENTS OR APPLICATIONS

| | | | |
|---|---|---|---|
| 1,055,842 | 1/1967 | United Kingdom | 260/513 R |

*Primary Examiner*—Dennis L. Albrecht
*Attorney, Agent, or Firm*—Kenneth F. Dusyn; James J. Farrell; Melvin H. Kurtz

[57] ABSTRACT

Mixtures of $C_6$–$C_{20}$ alkane and olefin sulphonates having better colour than mixtures of the individually produced detergent actives are prepared by subjecting an alpha-olefin feedstock to sequential sulphonation and sulphitation.

4 Claims, No Drawings

PRODUCTION OF ALKANE: OLEFIN SULFONATE MIXTURES BY SEQUENTIAL SULFONATION AND SULFITATION

This invention relates to processes for the preparation of detergent active materials for use in detergent formulations. The process is of particular value in the preparation of detergent actives, but has other advantages.

For certain purposes in the preparation of detergent formulations it is necessary to have a mixture of sulphonated and sulphitated alpha-olefins. The methods of subjecting alpha-olefins to both sulphonation and sulphitation individually are well known.

In a sulphonation process the olefin is contacted with a sulphonation agent, for example oleum or sulphur trioxide, and the resulting acid neutralised to give the salts of the acids. The sulphonate anions present will be a mixture of hydroxy sulphonates, alkene sulphonates and disulphonate species. The mixture will be referred to hereafter as an olefin sulphonate.

An alpha-olefin will react with the bisulphite ion in solution to form an alkane sulphonate $R(CH_2)_2SO_3H$ and a sulphinate-sulphonate $RCH(SO_2H)CH_2(SO_3H)$ where R is a $C_6$ to $C_{20}$ alkyl group. Both olefin and alkane sulphonates are known as detergent actives and the sulphonation and sulphitation techniques are well documented, for example UK Pat. Nos. 983056, 1078097, 1093103, 1072601, 913206.

A mixture of members of these two active classes is of use in the preparation of detergent bars for personal washing. UK patent specification No. 1,171,616 discloses examples of detergent bars including a mixture of this type. The weight ratio of the alkane sulphonate to alkene sulphonate in the detergent bars disclosed therein is between 4:1 and 2:3.

The invention provides a method of producing this desired mixture of actives in good yield and with an improved colour over a simple mixture of the two actives prepared separately. Because of the better colour achieved by the method of the invention, reduced quantities of a bleach will be required. In addition to a cost saving in the use of bleach, the concentration of inorganic species in the final product will be reduced. It is normally desirable to keep the concentration of these inorganic species as low as possible in any active system, because normally they form an inert proportion of the total formulations. Further, such inorganic species can have a deleterious effect on the properties of specific formulations, for example detergent bars.

In the process of the invention a feedstock of alpha-olefin is subjected to incomplete sulphonation to a desired level and then a sulphitation step in sequence. The reaction medium for the sulphitation may be the known mixture of water and a short chain alcohol, or water alone can be used. It will be appreciated that the mixture of olefin sulphonate and alkane sulphonate obtained will have the chain length distribution of the original feedstock. It is possible to vary the chain lengths between the alkane sulphonate and olefin sulphonate by the addition of furher feedstock of different chain length after the first sulphonation step. In this case the feedstock to the sulphitation step will include alpha-olefin of the original feedstock chain length and the chain length of the added material.

Preferably the alpha-olefin is sulphonated in a falling film reactor using an $SO_3$/air mixture containing from 2 to 4% $SO_3$ at a temperature of up to 80° C in the film. Preferably the sulphonation conversion is from 10% to 70%.

It has been found that the presence of the olefin sulphonate 'heel' in the material passing to the sulphitation stage increases the rate of sulphitation. This increase in rate allows smaller reactors to be used leading to an overall cost saving.

The process of the invention allows feedstock containing vinylidene olefin to be processed. Long chain vinylidene olefins do not sulphitate when treated with the bisulphite ion. Exceptions are the 2-methyl and 2-ethyl vinylidene olefins. It is therefore not possible to use many of the commercially available alpha-olefins for alkane sulphonate production since many of these contain varying amounts of vinylidene olefins. These vinylidene olefins can be removed by a special de-oiling process, but it will be appreciated that this increases the cost of the final product as well as removing olefinic material which could be of potential value in an active. Using the process of the invention, a vinylidene-containing olefin mixture can be first sulphonated when the vinylidene olefins react with the sulphonation agent, to form an olefin sulphonate reaction product, and subsequently sulphitated to form the alkane sulphonate derivative of the other remaining alpha-olefins. Commercial olefins normally contain a very small proportion of internal olefin; these are only amenable to incomplete sulphonation and do not sulphitate; therefore, the final product of the present invention will still retain a small concentration of internal olefin. Preferably the feedstock olefin is subjected to a pre-treatment, for example, that set out in UK patent specification No. 1,159,728.

The sulphitation step is usually performed at a pH between 6.5 and 8, preferably 7.3 to 7.5. At a lower pH, ie below 6.5, an alkane disulphonate or alkane sulphinate/sulphonate is formed in addition to the monosulphonate. These di-anionic species provide building action in the wash liquor.

The chain length of the olefinic feedstock is preferably in the range from $C_{11}$ to $C_{20}$. In a preferred process, a $C_{15}$ to $C_{18}$ feedstock is first subjected to sulphonation with sulphur trioxide/air in low conversion, ie about 70%. A quantity of $C_{11}/C_{14}$ feedstock is then added in a ratio of 2:3 wt/wt to the original $C_{15}/C_{18}$ feedstock. The whole is then subjected to sulphitation in an isopropanol/water reaction medium at a pH from 7.3 to 7.4.

Non-limiting examples will now be given to illustrate the invention.

EXAMPLE I

A charge of $C_{15-18}$ alpha-olefin (feed rate 20 lbs/hour) was subjected to sulphonation with an $SO_3$/air mixture (4% $SO_3$ by volume) in a falling film reactor. The resulting product was neutralised with sodium hydroxide solution (5%). The conversion was about 46% and the product that was passed to the sulphitation stage had the following analysis (by weight):

| | |
|---|---|
| Olefin sulphonate | 22.2% |
| Sodium sulphate | 0.4% |
| Sodium hydroxide | 0.4% |
| Water | 60.0% |
| Unreacted olefin | 17.0% |

1,500 g of the sulphonation product was mixed with $C_{11-14}$ alpha-olefin (486 g) and isopropanol (1,113 g). The whole was heated to reflux temperature (about 82° C) and stirred vogorously. An amount of a bisulphite solution was added to give a reaction medium with a pH of 7.3. The bisulphite solution contained sodium metabisulphite (318 g) and sodium hydroxide (31.6 g) dissolved in water (765 g). At this stage t-butyl perbenzoate (4.99 g) was added as initiator. As the sulphitation reaction progressed, bisulphite solution was added at a rate sufficient to keep the reaction medium pH in the range 7.3 to 7.4. When all the bisulphite solution had been added a small quantity (1.66 g) of the initiator was added and then sulphur dioxide passed at a rate sufficient to keep the pH within the desired range of 7.4–7.5. An EIL model 41B pH meter was used with a Pye Ingold EO2 dual electrode. This meter was calibrated at 80° C to a pH of 7.

After the stoichiometric amount of bisulphite had reacted, a regulated flow of air was passed until the bisulphite solution had been added in 0.2 mole excess, as determined by sodium mass balance. This mass balance was measured by titration with caustic soda solution and hydrochloric acid.

The reaction product was a mixture of $C_{15-18}$ olefin sulphonate (26%), $C_{11-18}$ alkane sulphonate (58%), $C_{11-18}$ alkane 1-sulphonate 2-sulphinate (5%) and $C_{11-18}$ alkane 1:2 disulphonate (11%). The product was used to make toilet bars. The product had a klett value of 180 at 5%, 4 cm compared with a value of 280 for a mixture of the separately produced actives.

Example II

Example I was repeated using olefin sulphonated to 46% conversion. The sulphitation was performed in an aqueous reaction medium. The sulphonation product (800 g) was mixed with $C_{11-14}$ alpha-olefin (260 g) and heated to a temperature in the range 80 to 85° C during reaction. Bisulphite solution was made up by dissolving sodium metabisulphite (169 g) and sodium hydroxide (13.7 g) in water (402 g). The bisulphite solution was added to the olefin sulphonate product in the same manner as in Example I together with amounts of sodium nitrate as initiator in a quantity sufficient to keep the reaction rate constant (total weight added 35.5 g). This use of initiator is different from that of Example I. The bisulphite was added in 0.2 mole excess. Air and sulphur dioxide were added to the reaction points described in Example I.

The reaction product was a mixture of $C_{15-18}$ olefin sulphonate (60%) and $C_{11-18}$ alkane sulphonate (33%) in admixture with some $C_{11-18}$ alkane 1-sulphonate 2-sulphinate (7%).

The product was used to make toilet bars. The product had a klett value of 180 at 5%, 4 cm compared with a value of 280 for a mixture of the separately produced actives.

What is claimed is:

1. A process for preparing a mixture of alkane and alpha-olefin sulfonates containing from 6 to 20 carbon atoms for use in detergent formulations, by sulphonation and sulphitation of an alpha-olefin feedstock characterized in that the total alpha-olefin feedstock containing from 6 to 20 carbon atoms is subjected to incomplete sulphonation with a conversion of from 10 to 70%, and sulphitation sequentially.

2. A process according to claim 1 wherein the alpha-olefin feedstock contains from 11 to 20 carbon atoms.

3. A process according to claim 1, wherein an alpha-olefin feedstock containing from 15 to 18 carbon atoms is sulphonated and then mixed with an alpha-olefin feedstock containing from 11 to 14 carbon atoms prior to sulphitation.

4. A process according to claim 1 wherein the ratio of alkane sulfonate to said alpha-olefin sulfonate in the final mixture is from about 4:1 to about 1:1.82.

* * * * *